US008876701B2

(12) United States Patent
Surti et al.

(10) Patent No.: US 8,876,701 B2
(45) Date of Patent: Nov. 4, 2014

(54) MEDICAL SYSTEMS, DEVICES AND METHODS FOR ENDOSCOPICALLY SUTURING PERFORATIONS

(75) Inventors: Vihar C. Surti, Winston-Salem, NC (US); Tyler Evans McLawhorn, Winston-Salem, NC (US); Travis Benton Johnson, Dobson, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1271 days.

(21) Appl. No.: 12/348,180

(22) Filed: Jan. 2, 2009

(65) Prior Publication Data

US 2009/0177031 A1 Jul. 9, 2009

Related U.S. Application Data

(60) Provisional application No. 61/018,786, filed on Jan. 3, 2008.

(51) Int. Cl.
*A61B 1/00* (2006.01)
*A61B 1/04* (2006.01)
*A61B 17/04* (2006.01)
*A61B 1/018* (2006.01)
*A61B 17/06* (2006.01)
*A61B 17/062* (2006.01)

(52) U.S. Cl.
CPC ..... *A61B 17/0469* (2013.01); *A61B 2017/0609* (2013.01); *A61B 17/0487* (2013.01); *A61B 17/0625* (2013.01); *A61B 17/0491* (2013.01); *A61B 1/018* (2013.01); *A61B 1/00087* (2013.01)
USPC ............................ 600/127; 600/104; 600/129

(58) Field of Classification Search
CPC .................................................. A61B 1/00089
USPC ........................... 600/104, 127, 129; 606/144
See application file for complete search history.

(56) References Cited

U.S. PATENT DOCUMENTS

| 1,037,864 | A | 9/1912 | Carlson |
| 2,880,728 | A | 4/1959 | Rights |
| 3,470,875 | A | 10/1969 | Johnson |
| 3,513,848 | A | 5/1970 | Winston et al. |
| 4,236,470 | A | 12/1980 | Stenson |

(Continued)

FOREIGN PATENT DOCUMENTS

| EP | 1946707 A2 | 7/2008 |
| JP | 2004 041733 A | 2/2004 |

(Continued)

OTHER PUBLICATIONS

Fritscher-Ravens, Transgastric endoscopy—a new fashion, a new excitement!, Article, Endoscopy 2007, pp. 161-167, vol. 39.

(Continued)

*Primary Examiner* — Alireza Nia
(74) *Attorney, Agent, or Firm* — Brinks Gilson & Lione (57) ABSTRACT

Medical systems, devices and methods are disclosed for suturing a perforation in tissue, that may be employed endoscopically and/or laparoscopically, and that offer simple, reliable and controllable placement of suture around a perforation for complete closure thereof. One embodiment of the medical system generally includes an endoscope, an endcap, a needle, a suture, and first and second grip systems configured for relative translation to selectively pass the needle between the first and second grip systems.

21 Claims, 9 Drawing Sheets

(56) References Cited

U.S. PATENT DOCUMENTS

| | | |
|---|---|---|
| 4,635,638 A | 1/1987 | Weintraub et al. |
| 4,890,615 A | 1/1990 | Caspari et al. |
| 5,015,250 A | 5/1991 | Foster |
| 5,053,043 A | 10/1991 | Gottesman et al. |
| 5,059,201 A | 10/1991 | Asnis |
| 5,222,508 A | 6/1993 | Contarini |
| 5,304,184 A | 4/1994 | Hathaway et al. |
| 5,320,632 A | 6/1994 | Heidmueller |
| 5,350,385 A | 9/1994 | Christy |
| 5,356,424 A | 10/1994 | Buzerak et al. |
| 5,364,408 A | 11/1994 | Gordon |
| 5,368,601 A | 11/1994 | Sauer et al. |
| 5,374,275 A | 12/1994 | Bradley et al. |
| 5,376,096 A | 12/1994 | Foster |
| 5,389,103 A | 2/1995 | Melzer et al. |
| 5,391,182 A | 2/1995 | Chin |
| 5,403,329 A | 4/1995 | Hinchcliffe |
| 5,405,354 A | 4/1995 | Sarrett |
| 5,417,699 A | 5/1995 | Klein et al. |
| 5,439,469 A | 8/1995 | Heaven et al. |
| 5,462,561 A | 10/1995 | Voda |
| 5,470,338 A | 11/1995 | Whitfield et al. |
| 5,476,469 A | 12/1995 | Hathaway et al. |
| 5,478,353 A | 12/1995 | Yoon |
| 5,562,683 A | 10/1996 | Chan |
| 5,562,688 A | 10/1996 | Riza |
| 5,571,090 A | 11/1996 | Sherts |
| 5,571,119 A | 11/1996 | Atala |
| 5,573,540 A | 11/1996 | Yoon |
| 5,578,044 A | 11/1996 | Gordon et al. |
| 5,586,986 A | 12/1996 | Hinchliffe |
| 5,643,292 A | 7/1997 | Hart |
| 5,645,552 A | 7/1997 | Sherts |
| 5,653,717 A | 8/1997 | Ko et al. |
| 5,683,402 A | 11/1997 | Cosgrove et al. |
| 5,700,273 A | 12/1997 | Buelna et al. |
| 5,728,113 A | 3/1998 | Sherts |
| 5,741,278 A | 4/1998 | Stevens |
| 5,746,751 A | 5/1998 | Sherts |
| 5,792,153 A | 8/1998 | Swain et al. |
| 5,824,010 A | 10/1998 | McDonald |
| 5,836,955 A | 11/1998 | Buelna et al. |
| 5,836,956 A | 11/1998 | Buelna et al. |
| 5,846,253 A | 12/1998 | Buelna et al. |
| 5,860,990 A | 1/1999 | Nobles et al. |
| 5,865,836 A | 2/1999 | Miller |
| 5,908,428 A | 6/1999 | Scirica et al. |
| 5,938,668 A | 8/1999 | Scirica et al. |
| 6,348,059 B1 | 2/2002 | Hathaway et al. |
| 6,355,050 B1 | 3/2002 | Andreas et al. |
| 6,719,763 B2 | 4/2004 | Chung et al. |
| 6,755,843 B2 | 6/2004 | Chung et al. |
| 6,966,916 B2 | 11/2005 | Kumar |
| 6,972,027 B2 | 12/2005 | Fallin et al. |
| 6,988,987 B2 | 1/2006 | Ishikawa |
| 6,997,931 B2 | 2/2006 | Sauer et al. |
| 7,063,710 B2 * | 6/2006 | Takamoto et al. ............ 606/144 |
| 7,081,124 B2 | 7/2006 | Sancoff et al. |
| 7,112,207 B2 | 9/2006 | Allen et al. |
| 7,118,583 B2 | 10/2006 | O'Quinn et al. |
| 7,122,039 B2 | 10/2006 | Chu |
| 7,122,040 B2 | 10/2006 | Hill et al. |
| 7,144,401 B2 | 12/2006 | Yamamoto et al. |
| 7,157,636 B2 | 1/2007 | Hsieh |
| 7,166,116 B2 | 1/2007 | Lizardi et al. |
| 7,175,636 B2 | 2/2007 | Yamamoto et al. |
| 7,232,448 B2 | 6/2007 | Battles et al. |
| 7,273,451 B2 | 9/2007 | Sekine et al. |
| 7,323,004 B2 | 1/2008 | Parihar |
| 7,326,221 B2 | 2/2008 | Sakamoto |
| 7,344,545 B2 | 3/2008 | Takemoto et al. |
| 7,527,590 B2 | 5/2009 | Suzuki et al. |
| 7,530,985 B2 | 5/2009 | Takemoto et al. |
| 7,575,548 B2 * | 8/2009 | Takemoto et al. ............ 600/104 |
| 7,585,308 B2 | 9/2009 | Weisenburgh, II et al. |
| 7,615,060 B2 | 11/2009 | Stokes et al. |
| 7,618,425 B2 * | 11/2009 | Yamamoto et al. ........... 606/139 |
| 7,628,796 B2 | 12/2009 | Shelton, IV et al. |
| 7,722,631 B2 | 5/2010 | Mikkaichi et al. |
| 7,731,727 B2 | 6/2010 | Sauer |
| 7,736,372 B2 | 6/2010 | Reydel et al. |
| 7,753,923 B2 | 7/2010 | St. Goar et al. |
| 7,766,925 B2 | 8/2010 | Stokes et al. |
| 7,776,066 B2 | 8/2010 | Onuki et al. |
| 2002/0116010 A1 | 8/2002 | Chung et al. |
| 2002/0116011 A1 | 8/2002 | Chee Chung et al. |
| 2002/0198542 A1 | 12/2002 | Yamamoto et al. |
| 2003/0009085 A1 | 1/2003 | Arai et al. |
| 2003/0045891 A1 | 3/2003 | Yamamoto et al. |
| 2003/0181924 A1 | 9/2003 | Yamamoto et al. |
| 2003/0216613 A1 | 11/2003 | Suzuki et al. |
| 2004/0097982 A1 | 5/2004 | Jugenheimer et al. |
| 2005/0090709 A1 | 4/2005 | Okada et al. |
| 2005/0143762 A1 | 6/2005 | Paraschac et al. |
| 2005/0149067 A1 | 7/2005 | Takemoto et al. |
| 2005/0251165 A1 | 11/2005 | Vaughan et al. |
| 2006/0155288 A1 | 7/2006 | Little et al. |
| 2006/0253144 A1 | 11/2006 | Mikkaichi et al. |
| 2006/0271073 A1 | 11/2006 | Lam et al. |
| 2006/0271101 A1 | 11/2006 | Saadat et al. |
| 2007/0093858 A1 | 4/2007 | Gambale et al. |
| 2007/0100375 A1 | 5/2007 | Mikkaichi et al. |
| 2007/0100376 A1 | 5/2007 | Mikkaichi et al. |
| 2007/0112362 A1 | 5/2007 | Mikkaichi et al. |
| 2007/0123840 A1 | 5/2007 | Cox |
| 2007/0191886 A1 | 8/2007 | Dejima et al. |
| 2007/0197864 A1 | 8/2007 | Dejima et al. |
| 2007/0198000 A1 | 8/2007 | Miyamoto et al. |
| 2007/0255296 A1 | 11/2007 | Sauer |
| 2007/0276424 A1 | 11/2007 | Mikkaichi et al. |
| 2008/0114378 A1 | 5/2008 | Matsushita |
| 2008/0114379 A1 | 5/2008 | Takemoto et al. |
| 2008/0172088 A1 | 7/2008 | Smith et al. |
| 2008/0177304 A1 | 7/2008 | Westra et al. |
| 2008/0243148 A1 | 10/2008 | Mikkaichi et al. |
| 2008/0262525 A1 | 10/2008 | Chang et al. |
| 2009/0069822 A1 | 3/2009 | Takahashi et al. |
| 2009/0125038 A1 | 5/2009 | Ewers et al. |
| 2009/0216081 A1 | 8/2009 | Suzuki et al. |
| 2009/0222027 A1 | 9/2009 | Sauer |
| 2009/0222029 A1 | 9/2009 | Gordin et al. |
| 2009/0223426 A1 | 9/2009 | Shonteff et al. |
| 2009/0299385 A1 | 12/2009 | Stefanchik et al. |
| 2009/0306686 A1 | 12/2009 | Ohdaira |
| 2009/0312773 A1 | 12/2009 | Cabrera et al. |
| 2009/0320861 A1 | 12/2009 | Taylor et al. |
| 2010/0010511 A1 | 1/2010 | Harris et al. |
| 2010/0010512 A1 | 1/2010 | Taylor et al. |
| 2010/0010520 A1 | 1/2010 | Takahashi et al. |
| 2010/0030028 A1 | 2/2010 | Cabrera et al. |
| 2010/0030238 A1 | 2/2010 | Viola et al. |
| 2010/0030239 A1 | 2/2010 | Viola et al. |
| 2010/0049213 A1 | 2/2010 | Serina et al. |
| 2010/0049219 A1 | 2/2010 | Cronin et al. |
| 2010/0057108 A1 | 3/2010 | Spivey et al. |
| 2010/0063521 A1 | 3/2010 | Manzo |
| 2010/0076460 A1 | 3/2010 | Taylor et al. |
| 2010/0076461 A1 | 3/2010 | Viola et al. |
| 2010/0094083 A1 | 4/2010 | Taylor et al. |
| 2010/0094341 A1 | 4/2010 | Raju |
| 2010/0113873 A1 | 5/2010 | Suzuki et al. |
| 2010/0160961 A1 | 6/2010 | Nawrocki et al. |
| 2010/0211082 A1 | 8/2010 | Sauer |
| 2010/0211083 A1 | 8/2010 | Sauer |
| 2010/0217282 A1 | 8/2010 | Cabrera et al. |

FOREIGN PATENT DOCUMENTS

| | | |
|---|---|---|
| WO | WO/93/01750 A | 2/1993 |
| WO | WO 01/01868 A | 1/2001 |

(56) References Cited

FOREIGN PATENT DOCUMENTS

WO WO 2004/103157 A 12/2004
WO WO 2008/045376 A 4/2008

OTHER PUBLICATIONS

Sclabas, et al., Endoluminal Methods for Gastrotomy Closure in Natural Orifice TransEnteric Surgery (NOTES), Article, Surgical Innovation, vol. 13, No. 1, Mar. 2006, pp. 23-30.

Bergström, et al., Early clinical experience with a new flexible endoscopic suturing method for natural orifice transluminal endoscopic surgery and intraluminal endosurgery (with videos), Article, Gastrointestinal Endoscopy vol. 67, No. 3, 2008, pp. 528-533.

Ryou, et al., Evaluation of a novel access and closure device for NOTES applications: a transcolonic survival study in the porcine model (with video, Article, Gastrointestinal Endoscopy, vol. 67, No. 6, 2008, pp. 964-969.

Moran, et al., Preliminary performance of a flexible cap and catheter-based endoscopic suturing system, Article Gastointestinal Endoscopy, vol. 69, No. 7, 2009, pp. 1375-1383.

Park, et al., Endoscopic sutured closure of a gastric natural orifice transluminal endoscopic surgery access gastrotomy compared with open surgical closure in a porcine model. A randomized, multicenter controlled trial, Article, Endoscopy 2010, vol. 42, pp. 311-317.

International Search Report/Written Opinion dated Aug. 19, 2009, PCT/US2009/030030.

International Preliminary Report on Patentability dated Feb. 1, 2010, PCT/US2009/030030.

International Search Report/Written Opinion dated Aug. 20, 2010, PCT/US2010/032929.

\* cited by examiner

MEDICAL SYSTEMS, DEVICES AND METHODS FOR ENDOSCOPICALLY SUTURING PERFORATIONS

CROSS-REFERENCE TO RELATED APPLICATIONS

This application claims the benefit of U.S. Provisional Application Ser. No. 61/018,786 filed on Jan. 3, 2008, entitled "MEDICAL SYSTEMS, DEVICES AND METHODS FOR ENDOSCOPICALLY SUTURING PERFORATIONS" the entire contents of which are incorporated herein by reference.

FIELD OF THE INVENTION

The present invention relates generally to medical systems, devices and procedures for suturing tissue, such as for endoscopically suturing perforations in tissue.

BACKGROUND OF THE INVENTION

Openings or perforations in the walls of internal organs and vessels may be naturally occurring, or formed intentionally or unintentionally. These openings may be used to gain access to adjacent structures of the body, such techniques being commonly referred to as transluminal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies or other operations, such as tubal ligation. Many transluminal procedures for gaining access to various body cavities using other bodily lumens have also been developed. Natural orifices such as the mouth, nose, ear, anus or vagina may provide access to such bodily lumens and cavities. The bodily lumen(s) of the gastrointestinal tract are often endoscopically explored and can be utilized to provide access to the peritoneal cavity and other body cavities, all in a minimally invasive manner.

Compared to traditional open surgery or laparoscopic surgery, transluminal procedures are less invasive by eliminating abdominal incisions (or other exterior incisions) and incision related complications, while also reducing postoperative recovery time, reducing pain, and improving cosmetic appearance. At the same time, there remain challenges to transluminal procedures, including providing a suitable conduit to the openings and body cavities, robust medical devices that are maneuverable via the conduit and operable within the body cavity, sterility of the conduit, maintaining insufflation of the body cavity, proper closure of the opening, and prevention of infection. For example, when an opening is formed in a bodily wall of the gastrointestinal tract, such as in the stomach or intestines, spillage of the stomach contents, intestinal contents or other bodily fluids into the adjacent body cavity can occur. Travel of bacteria laden fluids outside of the gastrointestinal tract may cause unwanted and sometimes deadly infection.

In order to permanently close naturally occurring, intentionally or unintentionally formed perforations and allow the tissue to properly heal, numerous medical devices and methods have been developed employing sutures, adhesives, clips, tissue anchors and the like. One such class of devices aims to endoscopically close perforations, such as those within the gastrointestinal tract. Accordingly, various medical devices have been proposed that attach to the endoscope to facilitate perforation closure. Some of these medical devices employ suction to orient the tissue for suturing or anchor placement, while others require the use of tissue graspers or other devices to orient the tissue.

BRIEF SUMMARY OF THE INVENTION

The present invention provides medical systems, devices and methods for suturing a perforation in tissue, that may be used endoscopically and/or laparoscopically, and that offer simple, reliable and controllable placement of sutures around a perforation for complete closure thereof. One embodiment of a medical system, constructed in accordance with the teachings of the present invention, generally includes an endoscope, an endcap, a needle, a suture, a first grip system and a second grip system. The endoscope has a working channel and defines a longitudinal axis. The endcap is fitted to a distal end of the endoscope. The needle has first and second opposing ends, and a suture is attached to the needle. The first grip system is slidably connected to the endcap for longitudinal translating and structured to selectively engage the needle. The second grip system is structured to selectively engage the needle, and slidably passes through one of the endcap and the working channel of the endoscope. The first grip system and second grip system are configured for relative longitudinal translation to selectively pass the needle between the first and second grip systems.

According to more detailed aspects, the second grip system preferably includes a control member extending through the working channel of the endoscope. The first grip system (and/or the second grip system) may have an adjustable gripping force. The first and second grip systems are longitudinally spaced apart and define a suture area therebetween. The grip systems preferably include an adjustable opening having a natural state that is sized to engage the needle, and which are manually adjustable to reduce the size of the adjustable opening.

One embodiment of a medical device, constructed in accordance with the teachings of the present invention, generally includes an endcap, a needle, a suture, a first grip system and a second grip system. The endcap defines an interior space sized to receive a distal end of the endoscope. The needle has first and second opposing ends and the suture is attached to the needle. The first grip system is structured to selectively engage the needle with a predetermined first gripping force, while a second grip system is longitudinally spaced from the first grip system and structured to selectively engage the needle with a second gripping force. The second grip system has an adjustable gripping force to modify the second gripping force between a first level and a second level. The first grip system and a second grip system are configured for relative translation to selectively pass the needle between the first and second grip systems.

According to more detailed aspects of the medical device, the second level of the second gripping force is greater than the first gripping force. The first level of the second gripping force is lower than the first gripping force. The first grip system may be a plate defining an adjustable opening. The first grip system may also include a pair of wires defining an adjustable space therebetween. The second grip system may be a collet having fingers, adjustable forceps or other structures providing an adjustable gripping force. The endcap preferably includes support structures for guiding the needle and/or guiding the slidable movement of the first grip system and/or the second grip system.

One embodiment of a method for suturing a perforation in tissue and also provided in accordance with the teachings of the present invention. An endoscope and a medical device, such as an embodiment of the medical device described above, are provided. The endcap of the medical device is fitted to a distal end of the endoscope. The endoscope and medical device are introduced to a first site proximate the perforation, wherein the first grip system is on a first side of the tissue and the second grip system is on a second side of the tissue. The first and second grip systems are translated relative to one another to pass the needle and suture from the first grip system, through the tissue, to the second grip system. The endoscope and medical device are moved to a second site proximate the perforation, and the first and second grip systems are again translated relative to one another to pass the needle and suture from the second grip system, through the tissue to the first grip system. According to further detailed aspects, the step of passing the suture through the tissue may be performed without withdrawing the endoscope and medical from a location proximate the perforation. Preferably, the suture is passed through the tissue in a purse-string fashion. The method also includes positioning the needle within the first grip system, and translating the first and second grip systems relative to one another to position the needle within the second grip system. The gripping force of the second grip system is then adjusted to exceed the first gripping force, and the first and second grip systems are translated relative to one another to pass the needle from the first grip system to the second grip system. The gripping force of the second grip system is adjusted to be less than the first gripping force, and the first and second grip systems are translated relative to one another to pass the needle from the second grip system to the first grip system.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

Figure 1:
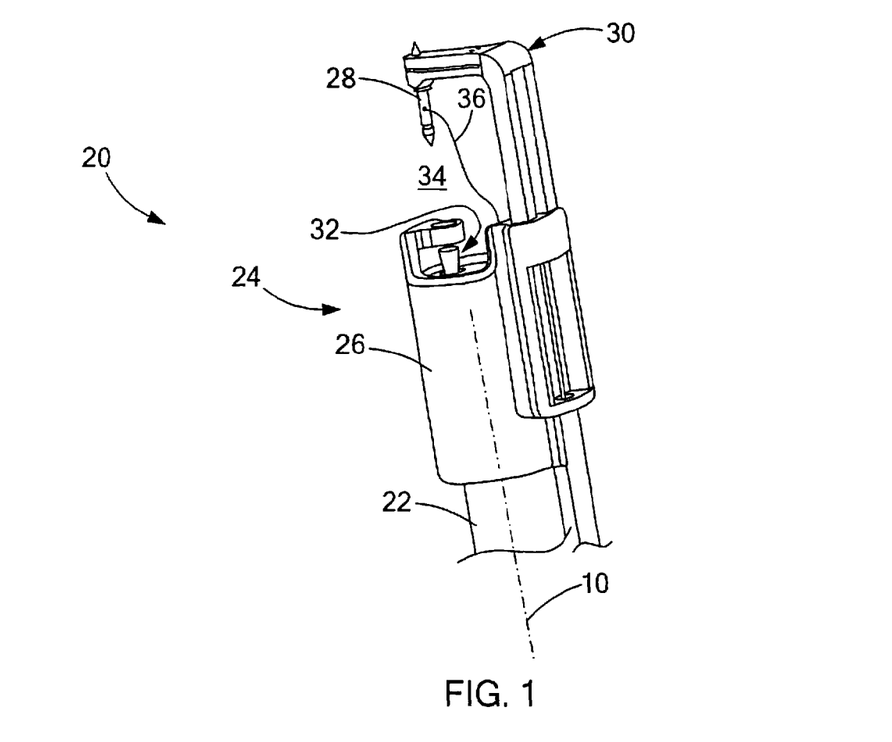
FIG. 1 is a perspective view of a medical system constructed in accordance to the teachings of the present invention.
Figure 2:
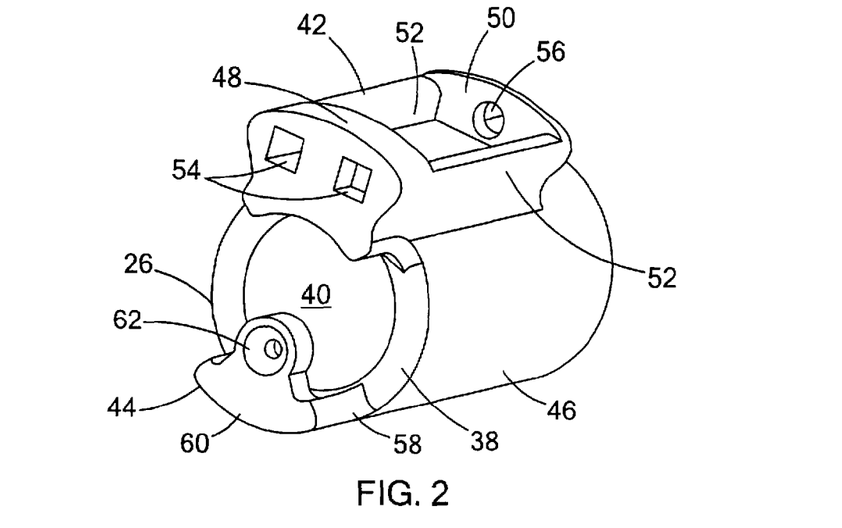
FIG. 2 is a perspective view of a portion of the medical system depicted in FIG. 1.
Figure 3:
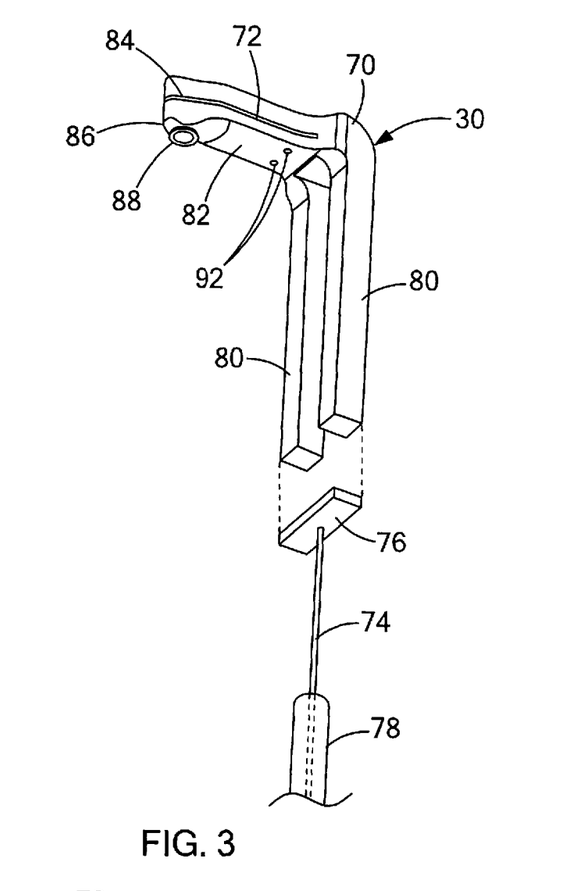
FIG. 3 is a perspective view of a portion of the medical system depicted in FIG. 1.

Turning now to the figures, FIGS. 1-3 depict a medical system 20 for suturing closed a perforation 14 in tissue 12 (shown in FIGS. 11-14), constructed in accordance with the teachings of the present invention. The medical system 20 generally comprises an endoscope 22 and a medical device 24 adapted for use with the endoscope 22. The endoscope 22 may be any scope known to those skilled in the art, and therefore may have various lengths, diameters and functionality. The endoscope 22 generally defines a central axis 10 which extends in a longitudinal direction. The medical device 24 generally includes an endcap 26, a needle 28, a distal grip system 30 and a proximal grip system 32. The distal and proximal grip systems 30, 32 are longitudinally spaced apart to define a suturing area 34. As will be later described with reference to FIGS. 8-13, tissue 12 is positioned within the suturing area 34, and the needle 28 is passed through the tissue 12, back-and-forth between the distal grip system 30 and the proximal grip system. A suture 36 is connected to the needle 28 such that the suture 36 is repeatedly passed through the tissue 12. In particular, the suture 36 is preferably woven through the tissue 12 around the perforation 14 in the tissue 12, whereby one end or both ends of the suture 36 may be used to draw the perforation 14 closed.

With reference to FIGS. 1 and 2, the endcap 26 includes a tubular body 38 defining an interior cavity 40 sized to be fitted on a distal end of the endoscope 22. The endcap 26 may be structured to frictionally engage the endoscope 22 for selective retention of the endcap 26 on the endoscope 22, although other means for connecting the endcap 26 to the endoscope 22 may be employed, as is known in the art. The endoscope 22 and medical device 24 are therefore adapted to be traversed through the body of a patient in this connected configuration shown in the figures.

As best seen in FIG. 2, the endcap 26 generally includes a first guide body 42 and a second guide body 44. The endcap 26 may be formed of various materials, preferably a plastic and more preferably a clear or translucent plastic such as SLA or other acrylic. The first guide body 42 is sized and structured to support and orient the distal gripping system 30, while the second guide body 44 is structured to guide and support the needle 28 relative to the proximal grip system 32. The first guide body 42 generally includes a distal guide flange 48, a proximal guide flange 50 and one or more reinforcing ribs 52 extending longitudinally between the distal and proximal guide flanges 48, 50. The distal guide flange 48 includes two passageways 54, and a proximal guide flange 50 includes a passageway 56, all of the passageways 54, 56 for slidably receiving portions of the distal grip system 30 therein. The second guide body 44 generally includes a support arm 58 and a guide flange 60 having a guide hole 62 therein. The guide hole 62 is preferably frustoconical, and tapers in the proximal direction for guiding the needle 28 therethrough towards the proximal grip system 32.

Figure 4:
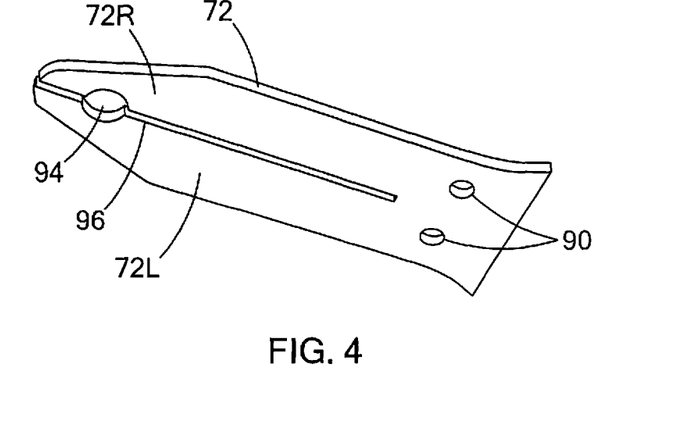
FIG. 4 is a perspective view of a portion of the medical system depicted in FIG. 1.

Turning now to FIGS. 3 and 4, the distal grip system 30 generally includes a gripping arm 70, a gripping plate 72, and a control wire 74. A connecting plate 76 may be used to connect the control wire 74 to the gripping arm 70 using any known means of mechanical connection such as soldering, welding, bonding, adhesives, fasteners or intercooperating mechanical structures such as tongue and grooves or tabs or detents etc. A sheath 78 is used to encase the control wire 74, the wire 72 being slidably received within the sheath 78. The sheath 78 extends to a proximal end of the endoscope 22 (not shown), where a proximal end of the sheath 78 may be accessed by the medical professional for manipulating the control wire 74. As the sheath 78 extends proximally along the endoscope 22, the sheath 78 has a length similar to the length of the endoscope 22, as does the control wire 74.

The gripping arm 70 generally includes one or more guide rods 80, two being shown in FIG. 3, and having a generally square cross-section. It will be recognized that the guide rods 80 are structured to be received within the passageways 54 of the distal guide flange 48. The guide rods 80 may have other cross-sectional shapes including rectangular, triangular, circular, trapezoidal or others. A gripping bracket 82 extends transversely from the guide rods 80 and defines a slot 84 sized and shaped to receive the gripping plate 72 (FIG. 4). The free end 86 of the gripping bracket 82 is atraumatically shaped as shown, and includes a guide hole 88 for receiving the needle 28. The guide hole 88 is preferably frustoconical in shape for guiding the needle 28 therein.

As shown in FIG. 4, the gripping plate 72 generally includes a gripping hole 94 sized to receive and engage the needle 28. In particular, the gripping hole 94 is adjustable in size by way of a slit 96 extending along the plate through gripping hole 94. As such, the slit 96 divides the gripping plate 72 into a right half 72R and left half 72L which may move relative to one another to adjust the size of the gripping hole 94. Preferably the gripping plate 72 is formed of a resilient material such as a metal or plastic that allows the size of gripping hole 94 to adjust. For example, stainless steel, alloys such as nitinol or aluminum, and thermoplastics may be used to form the gripping plate 72. Similar materials may also be used for the other parts of the upper grip system 30 including its gripping arm 70. A pair of attaching holes 90 are sized and positioned to cooperate with attaching holes 92 formed in the gripping bracket 82, through which a threaded fastener or other structure may be placed to connect the gripping plate 72 to the gripping bracket 82. As will be discussed in more detail herein, the distal grip system 30 and its gripping plate 72 are structured to grasp the needle 28 with a predetermined gripping force determined by the materials and structure of the plate 72, including the size of the gripping hole 94 and size (width and length) slit 96, as will be appreciated by those skilled in the art.

Figure 5:
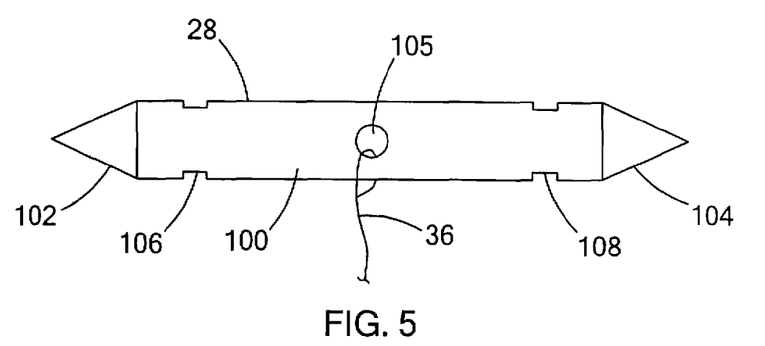
FIG. 5 is a side view of a needle forming a portion of the medical system depicted in FIG. 1.

Turning now to FIG. 5, the needle 28 is shown in detail. The needle includes an elongate body 100 having a first end 102 and second end 104 opposite the first end 102. The needle body 100 may be solid or hollow, and is preferably formed of a rigid material. Suitable materials for the needle 34 generally include metals such as stainless steel, alloys such as nitinol, plastics such as polyvinylchloride, polyimide, polyamide, polyetherketone and others known to those skilled in the art. The first and second ends 102, 104 of the needle body 100 are tapered to define a sharpened tip for piercing the tissue 12. An annular notch 106 is formed adjacent the first end 102, while a second annular notch 108 is formed adjacent the second end 104. Stated another way, the first and second notches 106, 108 define reduced diameter portions of the needle body 100 about which the distal grip system 30 and proximal grip system 32 may selectively engage the needle 100.

A connecting hole 105 is formed in the needle body 100 for connecting the suture 36 to the needle 28. The suture 36 may be connected via the hole 105 or otherwise, using various means, such as by tying, knots, adhesives, mechanical connectors (adjustable loops, clamps, etc.), bonding techniques such as plastic welding, melting, heat bonding and the like. Similarly, either the needle body 100 or the suture 36 may be mechanically deformed, such as by crimping or using other techniques, to interconnect the suture 36 and needle 28. One end of the suture 36 is attached to the needle 28, while the other end extends proximally along the endoscope 22 or through its working channel 23, as shown in FIG. 1.

Figure 6:
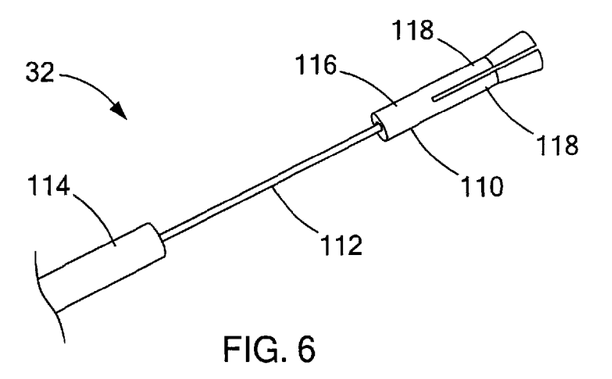
FIG. 6 is a perspective view of a portion of the medical system depicted in FIG. 1.
Figure 7:
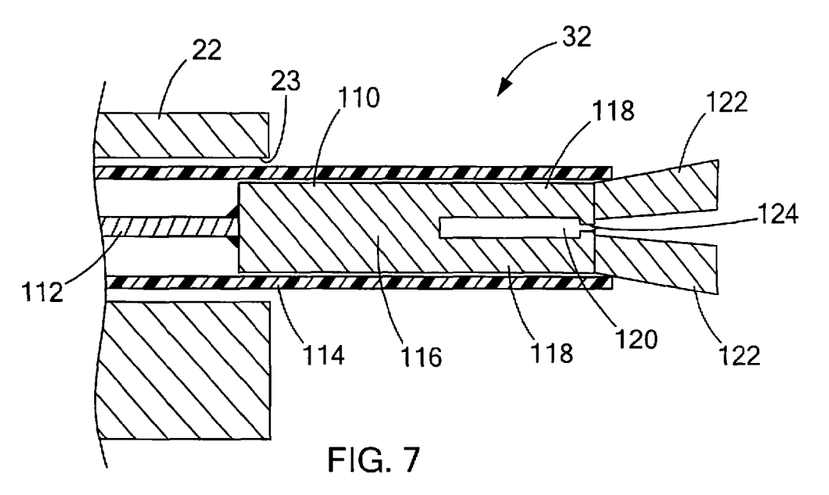
FIG. 7 is cross-sectional view of a portion of the medical system depicted in FIGS. 1 and 6.

The proximal grip system 32 is shown in FIGS. 6 and 7, and generally includes a control wire 112 slidably received within a catheter 114. The proximal grip system 32 further includes a collet 110 connected to a distal end of the control wire 112. The collet 110 includes a base 116 and a plurality of gripping fingers 118 as is known in the art. As best seen in FIG. 7, the collet 110 includes an internal space 120 sized to receive the needle 100 therein. The collet 110 is formed of a resilient material such as a metal or alloy, whereby the gripping fingers 118 are structured to adjust the size of the internal space 120. Distal ends 122 of the gripping fingers 118 are flared for guiding the needle 110 into the interior space 120, and inducing a compressive force on the gripping fingers 118 to reduce the size of the internal space 120. Teeth 124 may be formed on the interiors of the gripping fingers 118 proximate the interior space 120 for selectively engaging the slot 108 in the needle 100, although the teeth 124 and slot 108 may not be needed to operate the collet 110.

As best seen in FIG. 7, the proximal grip system 32 is sized to be received within the working channel 23 of an endoscope 22, and is translatable within the working channel 23. As such, the proximal grip system 32, and namely the control wire 112 and catheter 114, have a sufficient length to pass fully through to the working channel 23 of the endoscope 22 and exit a proximal end thereof (not shown) for manipulation by the medical professional. Either the working channel 23 or the catheter 114 may be used to press against the exterior of the collet 110, and in particular the flared distal ends 122 of the gripping fingers 118, to cause the interior space 120 to reduce its size and grasp the needle 28. Accordingly, the catheter 114 is preferably formed of polytetrafluorethylene (PTFE), expanded polytetrafluorethylene (EPTFE), polyethylene ether ketone (PEEK), polyvinylchloride (PVC), polycarbonate (PC), polyamide including nylon, polyimide, polyurethane, or polyethylene (high, medium or low density), including multi-layer or single layer constructions with or without reinforcement wires, coils or filaments.

Typically, the catheter 114 will be advanced over the control wire 112 (and/or the wire 112 is pulled proximally) to cause the grasping fingers 118 to collapse around the needle 28 with an adjustable gripping force. Preferably, the interior space 120 is sized and structured to naturally grip the needle 28 (such as through the teeth 124 and notch 118 or simply through frictional engagement) at a first level of the gripping force, and then the collet 110 and control wire 112 may be translated relative to the catheter 114 (or guide channel 23 of the endoscope 22) to provide an increase in the gripping force to a second level. As such, it will be recognized that the proximal grip system 32 provides an adjustable gripping force which may be controlled by the medical professional from the proximal end of the control wire 112 and catheter 114.

Figure 8:
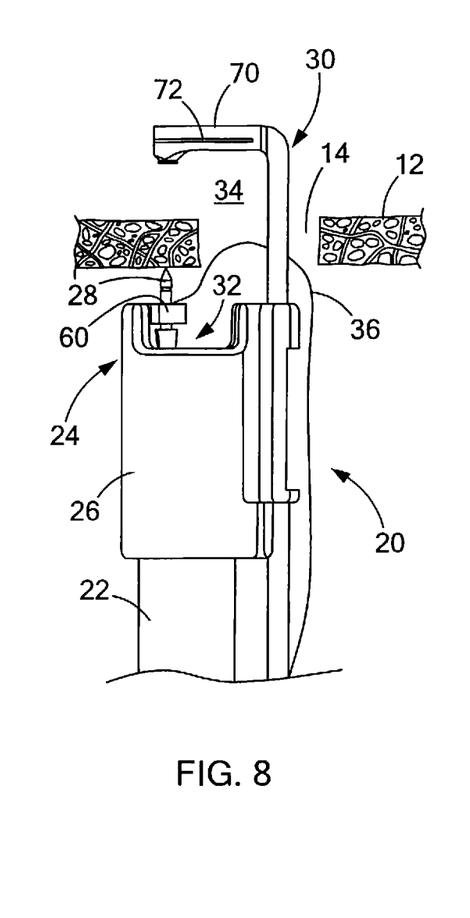
FIGS. 8-13 are front views, partially in cross-section, illustrating a method of employing the medical system depicted in FIG. 1.

As will now be described with reference to FIGS. 8-13, the medical system 20 may be used to suture close a perforation 14 formed in the tissue 12. The method of suturing the perforation 14 includes fitting the medical device 24, and namely its endcap 26, to a distal end of the endoscope 22. Preferably, the proximal grip system 32 is preloaded with the needle 28, although the needle 28 could be preloaded within the distal grip system 30. The medical system 20 is translated through the body to a position proximate the perforation 14. In particular, the endoscope 22 is used to visualize the tissue 12 and perforation 14, as well as the suturing space 34 between a distal and proximal grip systems 30, 32. The medical system 20 is manipulated such that the tissue 12 enters the suturing space 34, as shown in FIG. 8.

Figure 9:
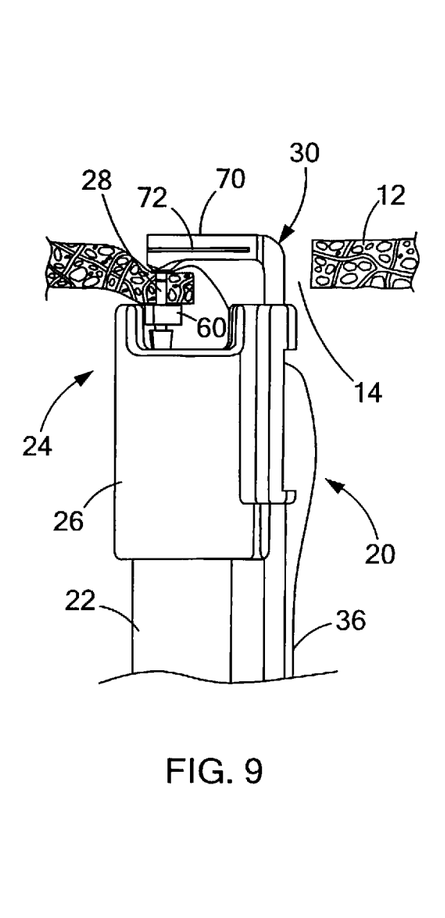
Figure 10:
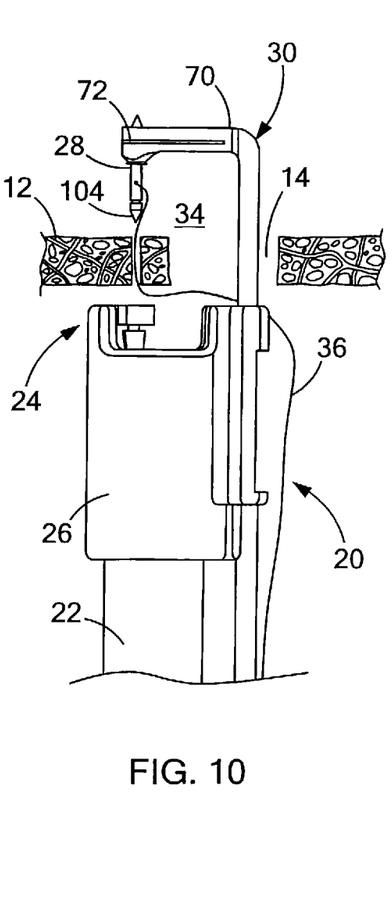

The distal grip system 30 and proximal grip system 32 are then translated relative to one another again (the proximal grip system 32 may be translated distally or the distal grip system 30 may be translated proximally, or both) such that the needle 28 passes through the tissue 12 and becomes engaged by the distal grip system 30 with its first gripping force, as shown in FIG. 9. In particular, the gripping hole 94 will increase in size to deflect the right and left portions, 72R, 72L of the gripping plate 72 until the hole 94 overlaps with the notch 106 formed in the body 100 of the needle 28 (see FIGS. 4 and 5). Then, the proximal grip system 32 is operated to reduce the second gripping force from its second level to its first level. That is, the control wire 112 and catheter 114 are translated relative to one another to reduce the force on the exterior of the collet 110 and to increase the size of the interior space 120 containing the needle 28. The first gripping force of the distal grip system 70 is generally greater than the first level of the second gripping force (of the proximal grip system 32), and therefore relative translation of the distal and proximal grip systems 30, 32 allows the needle 28 and suture 36 to be passed to the distal grip system 30, as shown in FIG. 10.

Figure 11:
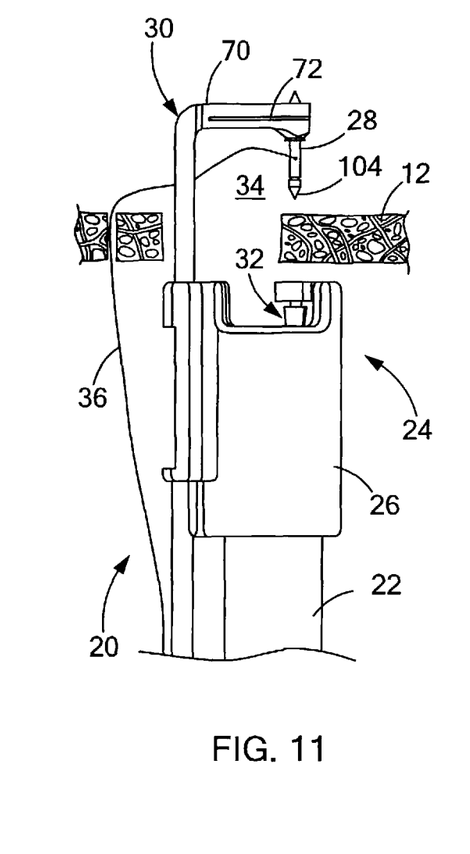
Figure 12:
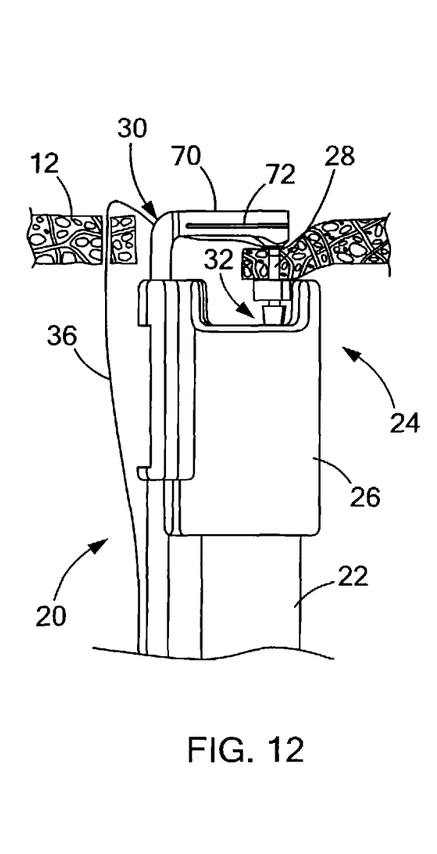
Figure 13:
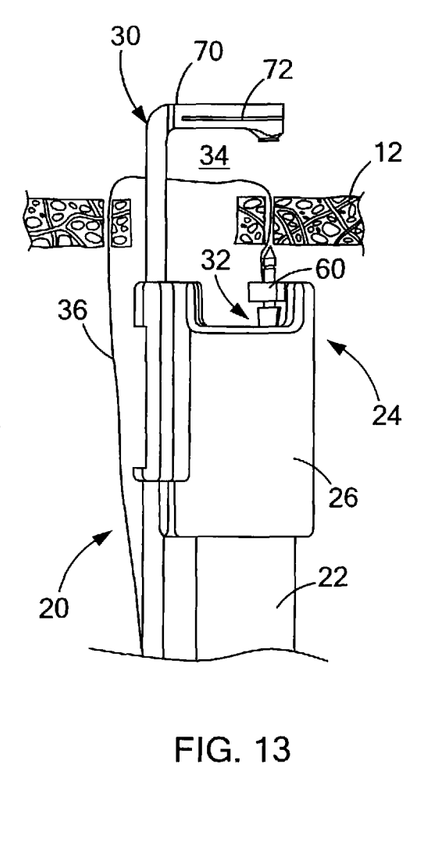

When the needle 28 and suture 36 have been passed through the tissue at least once, the medical system 20, and in particular the endoscope 22 is rotated from the first puncture site, as shown in FIG. 11. With the distal grip system 30 engaging the needle 28 with a first gripping force, the distal grip system 30 (or the proximal grip system 32 or both) is translated to again pass the needle 28 and the suture 36 through the tissue 12. The exposed end 104 of the needle 28 is moved through the guide hole 62 formed in the guide flange 60 of the endcap 26, until it can be grasped by the proximal grip system 32. In particular, the needle 28 enters the interior space 120 of the collet 110 (see FIG. 7) and is engaged with a second gripping force. As previously noted, the distal grip system 30 and its gripping plate 72 will engage the needle 28 with a first gripping force. Generally, the second gripping force is about equal to or less than the first gripping force. To transfer the needle 28, the proximal grip system 32 is activated through relative translation of the catheter 114 and control wire 112 (see FIG. 7) to increase the second gripping force from its first level to a second level. Generally, the second level of the second gripping force is greater than the first gripping force. Accordingly, the distal grip system 30 may be translated in a distal direction, and/or the proximal grip system 32 translated in a proximal direction, to again pass the needle 28 from the distal grip system 30 to the proximal grip system 32, as shown in FIG. 12.

Figure 14:
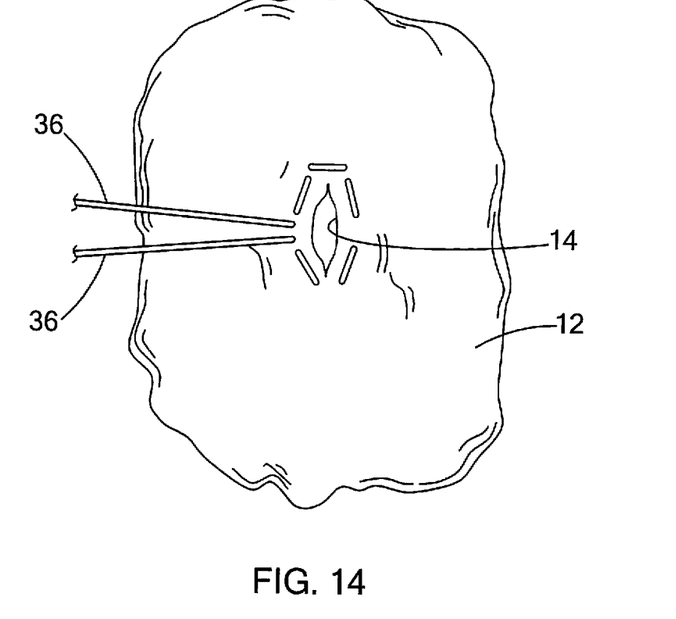
FIG. 14 is a plan view of tissue having a perforation being sutured using the medical system depicted in FIGS. 1-13.
Figure 15:
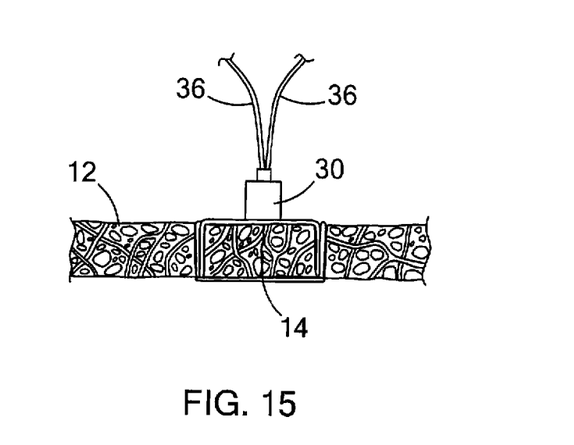
FIG. 15 is a cross-sectional view showing closure of the perforation and tissue depicted in FIG. 14.

In this manner, the suture 36 may be weaved through the tissue 12 and around the perforation 14 by repeating the above-described steps, as shown in FIG. 14. The suture 36 may follow a generally annular path round the periphery of the perforation 14, or may crisscross back and forth from opposing sides of the perforation 14. In either case, the medical system 20 is withdrawn from the patient, thereby withdrawing the needle 28 and one end of the suture 36. Accordingly, both ends of the suture 36 will be available to the medical professional and may be used to draw the perforation 14 closed, as shown in FIG. 15. Generally, the suture 36 has been passed through the tissue 12 in a purse-string fashion, whereby pulling proximally on the ends of the suture 36 will naturally cause the perforation 14 to close. The ends of the suture 36 may be tied utilizing endoscopic tying techniques including passing knots, or a suture lock 130 may be employed as is known in the art. Exemplary suture locks are described in U.S patent application Ser. No. 12/125,525 filed May 22, 2008 and Ser No. 12/191,001 filed Aug. 13, 2008, the disclosures of which are hereby incorporated by reference in their entirety.

Based on the foregoing it will be recognized by those skilled in the art that the medical systems, devices and methods of the present invention facilitate improved closure of perforations. The medical systems and devices are simple to operate, and the methods may be performed endoscopically and/or laparoscopically without removing the medical system 20 or device 24 every time a pass is made through the tissue. The devices and methods offer reliable and controllable placement of suture(s) around a perforation for complete and reliable closure thereof.

Figure 16:
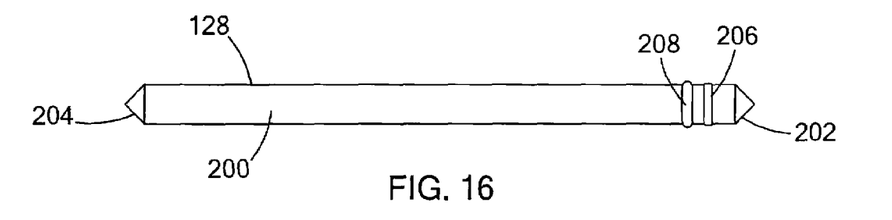
FIG. 16 is a front view of an alternate embodiment of the needle depicted in FIG. 5.

It will also be recognized that many variations of the medical system 20 and medical device 24 will be readily ascertainable to one of ordinary skill in the art. For example, the gripping structure of the distal grip system 30 and proximal grip system 32 may take many forms. Similarly, the needle 28 may also take many forms. One alternate construction of a needle 128 is shown in FIG. 16. In particular, the needle includes a needle body 200 and having a first end 202 and a second end 204 opposite the first end 202. At the first end 202, a first annular rib 206 and a second annular rib 208 are formed. Generally the first rib 206 has an outer diameter about the same size or larger than the gripping hole 94 formed in the gripping plate 72 of the distal grip system 30. Accordingly, the first rib 206 will cause enlargement of the gripping hole 94 but can pass therethrough. The second large rib 108 serves as a stop to positively locate the needle 28 longitudinally within the gripping plate 72. The second end 204 of the needle body 200 does not include a notch or other structure increasing/decreasing the diameter of the body 200, as the collet 110 of the proximal gripping system 32 is sufficient to grasp onto the needle 128 without the need for such gripping structures.

Figure 17:
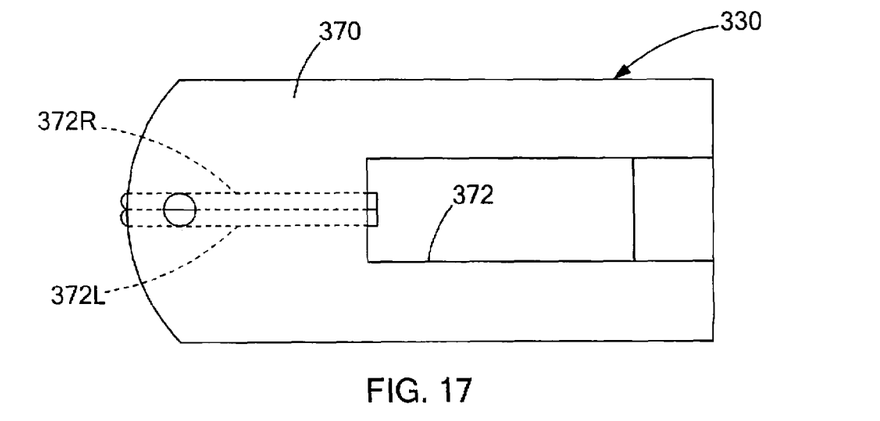
FIG. 17 is a plan view showing an alternate embodiment of a portion of the medical system depicted in FIGS. 3 and 4.

Turning now to FIG. 17, an alternate embodiment of the upper grip system 330 has been shown. In particular, the gripping arm 370 is substantially similar to the gripping arm 70 previously described with reference to FIG. 3, but the gripping plate 72 has been replaced by a pair of gripping wires 372R and 372L. The wires 372R and 372L are fixed to the gripping arm 370 within its slot 372 in a side-by-side fashion. The wires 372R and 372L will expand and increase the space therebetween as the needle 28 is being pushed through the wires. The wires should be formed of a resilient material by which they will return to their initial position once they reach the notch 106 formed in the needle 28 or when the needle 28 is removed.

Figure 18:
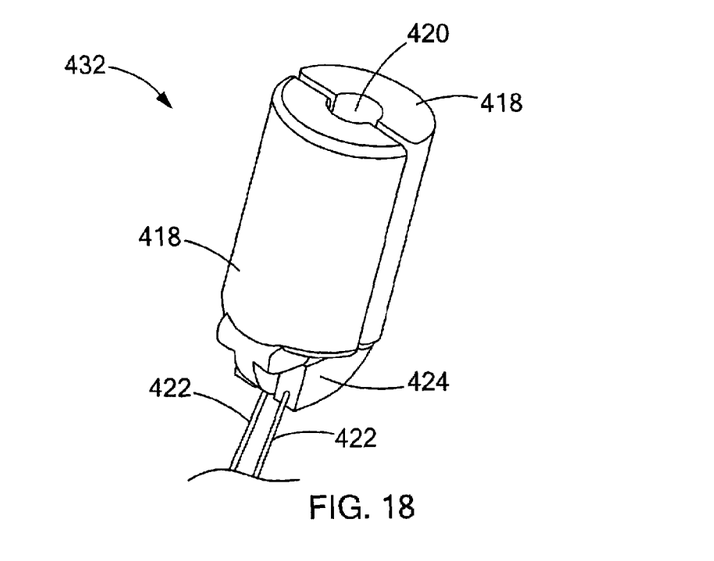
FIG. 18 is a perspective view of an alternate embodiment of a portion of the medical system depicted in FIGS. 6 and 7.

In FIG. 18, an alternate construction of a lower grip system 432 is shown. Generally, the proximal grip system 432 is an endoscopic forceps having opposing gripping fingers 418 defining a internal space 420 therein. Two control wires 422 are connected to the first and second gripping fingers 418, which are hinged together about pivot 424, in a scissors-like fashion to provide an adjustable gripping force between the fingers 418 for retaining the needle 28 within the interior space 420. It will be recognized that many other variations of the grip systems are possible, including the use of baskets, snares, loops, as well as employing magnets in the upper and lower grip systems 30, 32, in conjunction with the needle 28 being magnetized or formed with magnets embedded therein. Adjustability of magnet position or electromagnets may be employed to provide an adjustable gripping force. Further, either or both of the grip systems 30, 32 may function to apply an adjustable gripping force.

Figure 19:
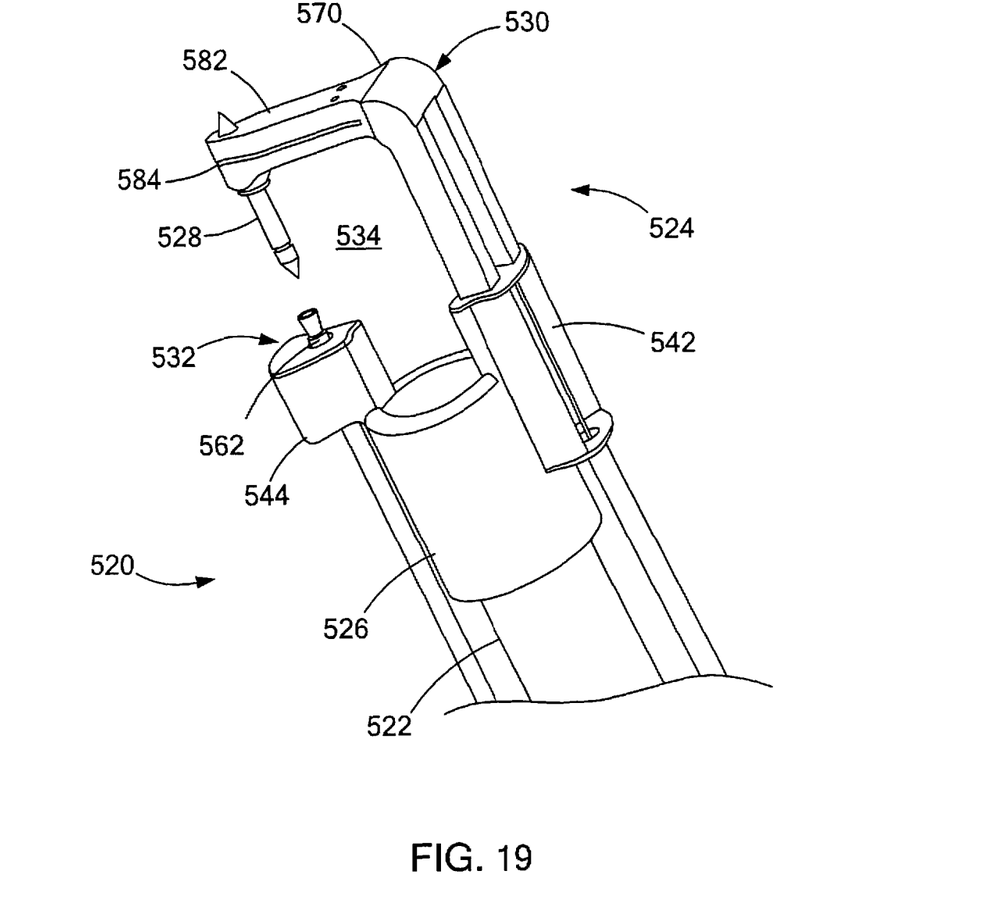
FIG. 19 is a perspective view of an alternate embodiment of the medical system constructed in accordance with the teachings of the present invention.

In FIG. 19, an alternate embodiment of a medical system 520, and in particular of the endcap 526, has been shown in accordance with the teachings of the present invention. The medical system generally includes an endoscope 522 and a medical device 524 attached to a distal end of the endoscope. The medical device 524 includes an endcap 526 having a first support body 542 and a second support body 544. The first support body 542 slidably supports the distal grip system 530, while the second support body 544 slidably supports the proximal grip system 532. In this embodiment, the second support structure 544 has positioned at or outside of the external surface of the endcap 526. Accordingly, the proximal grip system 532 is structured to extend along the exterior of the endoscope 522, rather than passing through a working channel thereof. Similarly, the distal grip system 530 includes a L-shaped arm 570 having a gripping bracket 582 and gripping plate 584 that are sized to extend a sufficient distance to be aligned with the proximal grip system 532. The proximal grip system 532 is supported by the second guide body 544 and extends through a guide hole 562 formed within the body 544. Accordingly, it will be recognized by those skilled in the art that in the embodiment of FIG. 19, the working channel of the endoscope 522 is not utilized by the medical device 524, and remains free for use of other instruments including cutting devices, grasping devices or any other useful tool known to those skilled in the art.

Figure 20:
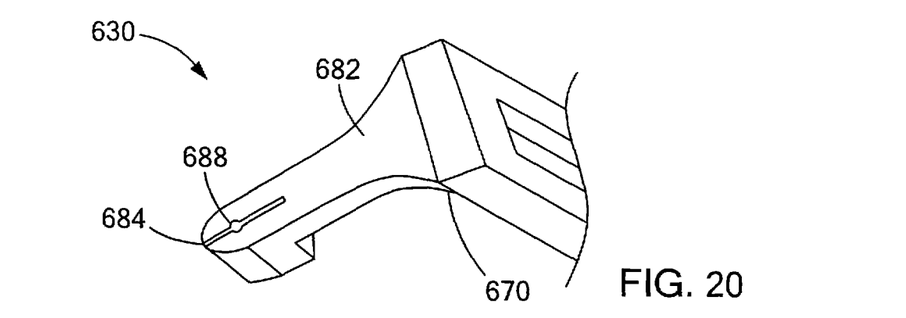
FIG. 20 is a perspective view showing an alternate embodiment of a portion of the medical system depicted in FIG. 3.

In FIG. 20, an alternate embodiment of the distal grip system 630 is shown. The distal grip system 630 generally includes a gripping arm 670, however the gripping plate (see, e.g. plate 72 in FIGS. 3 and 4) has been eliminated. In this embodiment, the gripping arm 670 includes a gripping bracket 682 that defines a slot 684 extending longitudinally through the gripping bracket 682 and has a width W. Coextensive with the slot 684 is a guide hole 688 for receiving the needle 28. The guide hole 688 has a predetermined diameter, while the slot 684 provides adjustability to the diameter of the guide hole 688 via flexure of the portions of the gripping bracket 682 separated by the slot 684. In this manner, the gripping arm 670 and its gripping bracket 682 provide a press fit or friction fit with the needle 28 for passing the needle through tissue. As discussed above, the distal grip system 630 and its gripping arm 670 are structured to grasp the needle 28 with a predetermined gripping force determined by the materials, size and structure of the gripping bracket 682, including the size of the gripping hole 688 and size (width and length) slot 684, as will be appreciated by those skilled in the art. It will also be recognized that the ends of the needle 28 may be flat and without a groove, while still capable of being gripped by the distal grip system 630.

Figure 21:
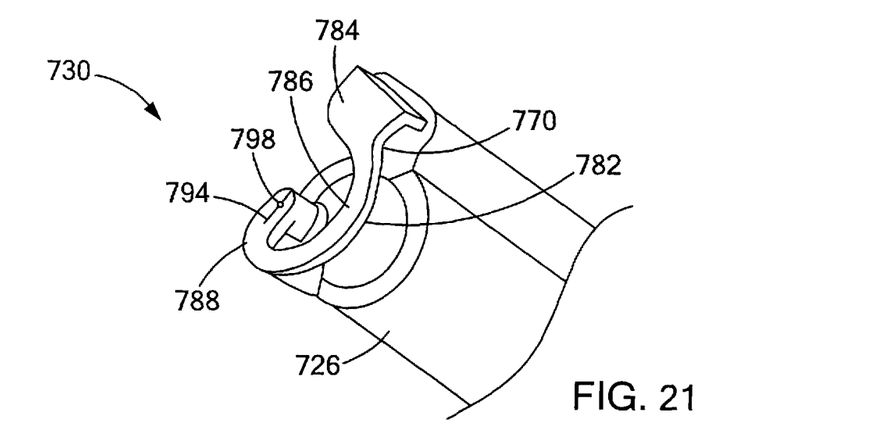
FIG. 21 is a perspective view showing another alternate embodiment of a portion of the medical system depicted in FIG. 3.
Figure 22:
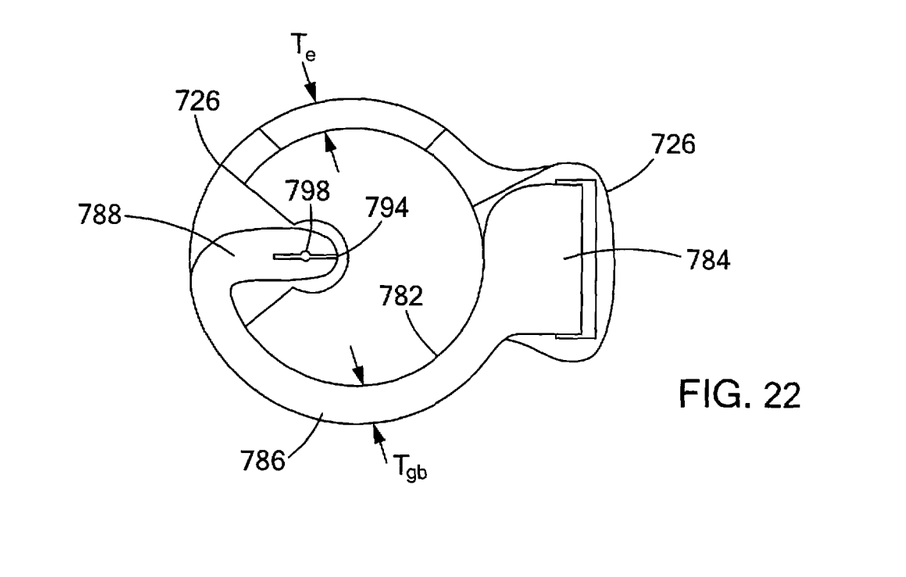
FIG. 22 is a plan view of FIG. 21.

In FIGS. 21-22, another alternate embodiment of the distal grip system 730 is shown. The distal grip system 730 generally includes a gripping arm 770 within an endcap 726 similar to previous embodiments, however in this embodiment gripping bracket 782 is curved to improve visibility through the endoscope. The gripping bracket 782 includes a first connecting portion 784, a second curved portion 786, and a third end portion 788. As best seen in FIG. 22, the second curved portion 786 is preferably formed to have a radius generally matching a radius of the endcap 726 and/or the endoscope (e.g. the radius of the inner surface of the second curved portion 786 may be about equal to an outer diameter of the endoscope). The second curved portion 786 also preferably has a thickness $T_{gb}$ about equal to a thickness $T_e$ of the wall of the endcap 726. As with the embodiment of FIG. 20, the third end portion 788 of the gripping bracket 782 may include a slot 794 and a gripping hole 798 sized to frictionally engage the needle 28 for passing it through tissue.

The foregoing description of various embodiments of the invention has been presented for purposes of illustration and description. It is not intended to be exhaustive or to limit the invention to the precise embodiments disclosed. Numerous modifications or variations are possible in light of the above teachings. In one variation, the distal grip system could be pivotally attached to the endcap and the needle driven through an arc via an actuating mechanism operated at a proximal end of the device. Appropriate guides, supports and the proximal grip system may be designed to pass the needle back and forth between the distal grip system. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical system for suturing a perforation in tissue, the medical system comprising:
   an endoscope having a working channel defined therein and defining a longitudinal axis;
   an endcap fitted to a distal end of the endoscope;
   a needle having a first end and a second end opposite the first end;
   a suture attached to the needle;
   a first grip system slidably connected to the endcap for longitudinal translation, in a longitudinal direction, the first grip system structured to selectively engage the needle;
   a second grip system structured to selectively engage the needle, the second grip system slidably passing through the working channel of the endoscope for longitudinal translation, the second grip system having an adjustable gripping force, the second grip system including a control member extending through the working channel of the endoscope; and
   the first grip system and second grip system configured for relative longitudinal translation to selectively pass the needle between the first and second grip systems, wherein the first grip system includes a rod slidably passing through a passageway formed in the endcap.

2. The medical system of claim 1, wherein the second grip system includes an adjustable opening radially aligned with the working channel.

3. The medical system of claim 1, wherein the second grip system is a collet having flexible fingers sized and positioned to circumferentially surround the needle.

4. The medical system of claim 3, wherein the first grip system has a non-adjustable gripping force.

5. The medical system of claim 4, wherein the first grip system includes an adjustable opening having a natural state that is sized to engage the needle.

6. The medical system of claim 5, wherein the needle includes a first notch proximate the first end, and wherein the natural state of the opening is sized to receive the needle about the first notch.

7. The medical system of claim 1, wherein the second grip system includes an adjustable opening having a natural state that is sized to engage the needle.

8. The medical system of claim 7, wherein the second grip system is manually adjustable to reduce the size of the adjustable opening.

9. The medical system of claim 1, wherein the second grip system is longitudinally spaced from the first grip system and radially aligned with the first grip system.

10. The medical system claim 1, wherein the first grip system selectively engages the needle with a predetermined first gripping force and the second grip system selectively engages the needle with an adjustable second gripping force that is adjustable between a first level and a second level, wherein the first level of the second gripping force is lower than the first gripping force, and wherein the second level of the second gripping force is greater than the first gripping force.

11. The medical system of claim 1, wherein the first grip system includes a flat plate defining an adjustable opening.

12. The medical system of claim 10, wherein the second grip system includes catheter, and wherein relative translation between catheter and collet adjusts the second gripping force between the first and second levels.

13. The medical system of claim 1, wherein the first grip system includes an L-shaped gripping arm slidably attached to an outer portion of endcap and defining an open distal end of the medical system.

14. The medical system of claim 13, wherein the L-shaped gripping arm includes a frustoconical opening to guide the needle.

15. The medical system of claim 1, wherein the endcap includes support arm for the second grip system, the support arm including guide hole radially aligned with a gripping member of the second grip system.

16. The medical system of claim 1, wherein the first grip system is a gripping member formed of a resilient material and having a slot extending laterally through the gripping member and opening on one lateral side of the gripping member, the gripping member further having a gripping hole extending longitudinally and passing through a middle portion of the slot and sized and positioned to receive the needle, the resilient material of the gripping member flexing to adjust the size of the gripping hole.

17. The medical system of claim 9, wherein a radial position of the second grip system relative to the longitudinal axis is fixed such that it is always radially aligned with the first grip system.

18. The medical system of claim 1, wherein the endcap includes an open distal end that does not enclose the endoscope.

19. The medical system of claim 1, wherein the first grip system includes a first guide arm projecting longitudinally and laterally from the endcap, and wherein the endcap and first guide arm are connected such that the first guide arm cannot rotate relative to the endcap.

20. A medical system for suturing a perforation in tissue, the medical system comprising:
    an endoscope having a working channel defined therein and defining a longitudinal axis;
    an endcap fitted to a distal end of the endoscope;
    a needle having a first end and a second end opposite the first end;
    a suture attached to the needle;
    a first grip system slidably connected to the endcap for longitudinal translation, in a longitudinal direction, the first grip system structured to selectively engage the needle;
    a second grip system structured to selectively engage the needle, the second grip system slidably passing through the working channel of the endoscope for longitudinal translation, the second grip system having an adjustable gripping force, the second grip system including a control member extending through the working channel of the endoscope; and
    the first grip system and second grip system configured for relative longitudinal translation to selectively pass the needle between the first and second grip system, wherein the first grip system includes an L-shaped gripping arm slidably attached to the endcap and defining an open distal end of the medical system, wherein the L-shaped gripping arm includes a guide rod extending longitudinally and a guide flange extended radially, the guide flange having a curved portion having a shape corresponding to a diameter of the endcap and that is sized and structured to permit_unobstructed viewing beyond the gripping arm with the endoscope.

21. The medical system of claim 20, wherein the curved portion of the gripping arm has a radius matching a radius of one of the endcap and the endoscope.

* * * * *